US011369718B1

(12) United States Patent
Pace

(10) Patent No.: US 11,369,718 B1
(45) Date of Patent: Jun. 28, 2022

(54) METHOD AND USE OF CRYOPRESERVED MESENCHYMAL STEM CELLS VIA LIQUID SUSPENSION FROM THE AMNIOTIC SAC FOR REJUVENATION OF THE MIDFACE

(71) Applicant: Ariasa LLC, Charlotte, NC (US)

(72) Inventor: Alissa Davis Pace, Charlotte, NC (US)

(73) Assignee: Ariasa LLC, Charlotte, NC (US)

( * ) Notice: Subject to any disclaimer, the term of this patent is extended or adjusted under 35 U.S.C. 154(b) by 327 days.

(21) Appl. No.: 16/548,149

(22) Filed: Aug. 22, 2019

Related U.S. Application Data

(60) Provisional application No. 62/722,590, filed on Aug. 24, 2018.

(51) Int. Cl.
| | |
|---|---|
| *A61K 35/50* | (2015.01) |
| *A61L 27/38* | (2006.01) |
| *A61L 27/36* | (2006.01) |
| *A61K 9/00* | (2006.01) |

(52) U.S. Cl.
CPC ........ *A61L 27/3804* (2013.01); *A61K 9/0019* (2013.01); *A61K 35/50* (2013.01); *A61L 27/3616* (2013.01); *A61L 27/3834* (2013.01); *A61L 27/3839* (2013.01); *A61L 2300/402* (2013.01); *A61L 2400/06* (2013.01); *A61L 2430/34* (2013.01); *A61L 2430/40* (2013.01)

(58) Field of Classification Search
None
See application file for complete search history.

(56) References Cited

U.S. PATENT DOCUMENTS

| 5,712,252 A | 1/1998 | Smith | |
|---|---|---|---|
| 9,974,840 B2 | 5/2018 | Bhatia et al. | |
| 2012/0264190 A1* | 10/2012 | Christman | A61P 29/00 435/405 |
| 2013/0072903 A1* | 3/2013 | Chapman | A61P 7/04 604/522 |
| 2016/0016015 A1* | 1/2016 | Slayton | A61H 23/0245 601/3 |
| 2017/0055561 A1* | 3/2017 | Naughton | A61P 1/00 |
| 2017/0216195 A1* | 8/2017 | Ames | A61K 9/0019 |

OTHER PUBLICATIONS

Spira et al. "Human amnion collagen for soft tissue augmentation—biochemical characterizations and animal observations", 1994, J of Biomedical Mat Research, vol. 28: 91-94 (Year: 1994).*
Anderson et al. "Surgical Treatment of Peroneus Brevis Tendon Repair with and without Human Amniotic Allograft: A Comparison Study." Clin. Surg. 2(2017): 1-5.
Bitterman-Deutsch et al. "Delayed immune mediated adverse effects to hyaluronic acid fillers: report of five cases and review of the literature." Dermatol. Reports. 6(2015): 5851.
Buday et al. "Evaluation of folded amniotic membrane and injectable amniotic memebrane pieces as soft tissue filler materials." Auris Nasus Larynx. 46(2019): 451-456.
Carruthers et al. "A validated facial grading scale: The future of facial ageing measurement tools?" J. Cosmet. Laser Ther. 12.5(2010): 234-241.
Davis et al. "Amniotic Allograft Implantation for Midface Aging Correction: A Retrospective Comparative Study with Platelet-Rich Plasma." Aesth. Plast. Surg. 43(2019): 1345-1352.
Di Germanic et al. "Amniotic Epithelial Cells: A New Tool to Combat Aging and Age-Related Diseases?" Front. Cell Dev. Biol. 4(2016): 135.
Friel et al. "Amniotic Fluid, Cells, and Membrane Application." Oper. Tech. Sports Med. 25(2016): 20-24.
Gassner et al. "Surgical Anatomy of the Face." Arch. Facial Plast. Surg. 10.1(2008): 9-19.
Hom et al. "The Healing Effects of Autologous Platelet Gel on Acute Human Skin Wounds." Arch. Facial Plast. Surg. 9.3(2007): 174-183.
Ilancheran et al. "Stem Cells Derived from Human Fetal Membranes Display Multilineage Differentiation Potential." Biol. Reproduct. 77(2007): 577-588.
Kaur et al. "Analysis of facial soft tissue changes with aging and their effects on facial morphology: A forensic perspective." Egypt. J. Forensic Sci. 5(2015): 46-56.
Kevy et al. "Comparison of Methods for Point of Care Preparation of Autologous Platelet Gel." JECT. 36(2004): 28-35.
Kim et al. "Clinical Implication of Allogenic Implantation of Adipogenic Differentiated Adipose-Derived Stem Cells." SCTM. 3(2014): 1312-1321.
Knight et al. "Tissue Engineering: Progress and Challenges." Plast. Reconstruct. Surg. 114(2004): 26E-37E.
Miki et al. "Stem Cell Characteristics of Amniotic Epithelial Cells." Stem Cells. 23(2005): 1549-1559.
Niknejad et al. "Properties of the Amniotic Membrane for Potential Use in Tissue Engineering." Eur. Cells Mater. 15(2008): 88-99.
ReNu™. Allograft Tissue Information and Product Preparation Insert. NuTech Medical, Inc. (2012).
Sclafani et al. "Modulation of Wound Response and Soft Tissue Ingrowth in Synthetic and Allogeneic Implants With Platelet Concentrate." Arch. Facial Plast. Surg. 7.3(2005): 163-169.
Shimberg. "The Use of Amniotic-Fluid Concentrate in Orthopaedic Conditions." Bone Joint Surg. 20(1938): 167-177.
Thomson et al. "Embryonic Stem Cell Lines Derived from Human Blastocysts." Science. 282(1998): 1145-1147.
Vines et al. "Cryopreserved Amniotic Suspension for the Treatment of Knee Osteoarthritis." J. Knee Surg. 29.6(2015): 443-450.

(Continued)

*Primary Examiner* — Teresa E Knight

(74) *Attorney, Agent, or Firm* — Womble Bond Dickinson (US) LLP; Deborah M. Vernon

(57) ABSTRACT

The present technology relates to a method of augmenting soft facial tissue in a human subject using a liquid suspension including amnion allograft. Analysis of the changes to midface volume, specifically the Ogee curve, observed in the chronological progression of photographs illustrates aesthetic improvements in both Platelet Rich Plasma (PRP) and amnion allograft treatment groups, with changes in the facial grading scale. Less patient downtime and slightly more rapid improvements were noted in the amnion group in comparison to PRP treatment participants. As a result, the amnion allograft provides advantages over the PRP procedure.

20 Claims, 11 Drawing Sheets

(56) References Cited

OTHER PUBLICATIONS

Werber et al. "A Prospective Study of 20 Foot and Ankle Wounds Treated with Cryopreserved Amniotic Membrane and Fluid Allograft." J. Foot Ankle Surg. 52.5(2013): 615-621.
Yu. "Human Amniotic Fluid-Derived and Amniotic Membrane-Derived Stem Cells." Stem Cells: Basics and Clinical Translation. Zhao, ed. 13(2015): 29-66.

* cited by examiner

Allograft before

Allograft post 12 weeks

Allograft before

Allograft post 12 weeks

US 11,369,718 B1

METHOD AND USE OF CRYOPRESERVED MESENCHYMAL STEM CELLS VIA LIQUID SUSPENSION FROM THE AMNIOTIC SAC FOR REJUVENATION OF THE MIDFACE

RELATED APPLICATIONS

This application claims the benefit of U.S. Provisional Application 62/722,590 filed on Aug. 24, 2018, the contents of which is incorporated herein by reference in its entirety.

FIELD OF THE TECHNOLOGY

The present disclosure relates to methods and procedures for rejuvenation of the midface by liquid injection. In particular, the present disclosure relates to injecting mesenchymal stem cells in a liquid suspension from the amniotic sac (for example, an amnion allograft) for the aesthetic rejuvenation of the midface.

BACKGROUND

Regenerative medicine has become more popular in aesthetics with the use of autologous cells, derived from a patient's own adipose cells and platelet rich plasma, for the potential tissue proliferation from various growth factors and mesenchymal stem cells. Amniotic allografts are becoming more popular for use in soft tissue growth in many areas of medicine because of their immunoprivilege that allows them to proliferate into tissues without rejection by the host. Mesenchymal stem cells (MSCs) have demonstrated ability to regenerate by direct tissue differentiation. Even more therapeutic properties have been identified including immunomodulation. See for example, Reference Number 4. A variety of molecules, including growth factors, are released from mesenchymal stem cells in response to injury. The mesenchymal stem cells of the amniotic membrane suppress inflammatory response when the cells release anti-inflammatories that suppress specific pro-inflammatory markers, such as transforming growth factor beta (TGF-$\beta$) associated specifically with a fibrotic response that leads to scar formation. Unique to the amniotic tissues are a form of hyaluronic acid (HA) called heavy chain HA.

Amniotic mesenchymal and epithelial cells release growth factors including epidermal growth factor, keratinocyte growth factor, and hepatocyte growth factor, with all being involved in the epithelialization and wound healing. Additionally, they facilitate the migration of the cells but also adhere to the basement membrane. Amniotic tissues have antimicrobial properties, molecules such as transferrin that may contribute to decreased infection risk with their presence. The extracellular matrix of the amniotic membrane includes laminin, heavy chain hyaluronic acid and collagen that are associated with scaffolding in tissue engineering. The minimal immune response can be attributed to the lack of human leukocyte antigen-A (HLA-A), human leukocyte antigen-B (HLA-B) and human leukocyte antigen-DR (HLA-DR) and is a unique characteristic to the placental membranes.

The clinical application of allogenic cells from amniotic tissue has been used in medical practice for over a century with its first documented use in soft tissues for treatment of burns. The use of amniotic allografts for orthopedic purposes dates back to 1938. See for example, Reference Number 15. The Werber and Martin 2013 prospective study of diabetics with chronic soft tissue wounds treated with amnion allografts showed 90% healing of wounds in 12 weeks without progression to amputation. The researchers attributed the favorable outcome of treatment with amnion allografts to its ability to fill soft tissue, as well as its anti-inflammatory and antimicrobial capabilities. See, for example, Reference Number 21.

Autologous cells, such as platelet rich plasma (PRP), are an excellent source for tissue engineering with low risk of immune complications. PRP has crossed over from wide orthopedic uses to the aesthetic market for hair restoration and midface volume replacement, owning, in part, to the minimal risk associated with the procedure and the convenience of in-office application. In addition, growth factors provided by PRP help stimulate collagen synthesis in the aging face. However, the potential recruitment of the patient's own mesenchymal stem cells to the PRP injection site would produce the most favorable and sustained aesthetic outcome. Limitations exist however, due to the quality of the source's cells particularly chronological age. Furthermore, underlying conditions of the source patient may lack in growth factors and inhibit the potential migration of mesenchymal stem cells to the area of PRP injection. The use of allogenic cells for tissue engineering offers uniformity, standardization of procedure, and quality control when compared to autologous cells used in other medical disciplines. See for example, Reference Number 11.

SUMMARY OF THE TECHNOLOGY

In general, the technology of the present disclosure is directed to midface rejuvenation by injection. In particular, methods and processes of the present technology are directed to the use of amnion allograft to augment a patient's appearance. Embodiments feature the use of liquid injections including amnion allograft to be delivered to specific regions of fat in the midface.

In one aspect, the technology is directed to a method of augmenting facial tissue in a human subject using a thawed liquid suspension comprising cryopreserved amnion allograft. The method includes injecting a first portion of the liquid suspension into a malar fat pad of the human subject followed by injecting a second portion the liquid suspension into the subcutaneous fat lying superior to the malar fat pad.

Embodiments of this aspect of the technology can include one or more of the following features. In one embodiment of the method, the liquid suspension is formed by thawing amnion allograft and mixing equal portions of thawed amnion allograft and saline. In certain embodiments, the first portion of the liquid suspension is injected into the superior lateral region of the malar fat pad. In further embodiments, the liquid suspension can be divided into a third portion. The third portion can be injected into reticular dermis proximate to the zygomatic arch area. In certain embodiments, a 21 to 23-gauge needle (e.g., 22-gauge needle) is used for the injections. In addition, in certain embodiments, the liquid suspension can be stored in a barrel capped with an injection needle and the entirety of the liquid suspension is injected prior to retracting the injection needle from the facial tissue of the human subject. In some embodiments, the first portion of the liquid suspension has a volume of 0.5 cc and the second portion of the liquid suspension has a volume of 0.4 cc. In embodiments including a third portion of liquid suspension, the volume of the third portion is 0.1 cc. After injection of the liquid suspension, certain embodiments of the method include applying pressure to an injection site immediate after retracting the needle from the facial tissue. In some embodiments, the method features a slow injection of the first portion of the liquid suspension (e.g., at least 25 seconds, at least 30 seconds, at least 35 seconds). In some embodiments of the method, a topical number agent is applied to the facial tissue of the human subject and removed prior to injecting the liquid suspension. In some embodiments, the liquid suspension is formed and injected within 30 minutes of removing frozen amnion allograft material from a freezer, ice or cryogenic storage container. In particular embodiments, a total injection time is under four minutes. And in some embodiments, the liquid suspension is injected in an in-office procedure under 1 hour (e.g., 30 minutes). In particular, the liquid suspension is injected in an in-office procedure with substantial recovery of the human subject within 1 hour (e.g., 45 minutes, 30 minutes). In general, substantial recovery of the human subject means the time needed for the patient to leave a practitioner's office after injection (e.g., after application of ice and pressure).

In another aspect, the technology is directed to a method of augmenting facial tissue in a human subject. The method of this aspect includes: forming a liquid suspension including thawing frozen amnion allograft for no more than 10 minutes and mixing the thawed amnion allograft with saline; injecting the liquid suspension within 20 minutes of thawing the frozen amnion allograft, wherein a first portion of the liquid suspension is injected into medial to lateral malar fat pad region adjacent to the lateral canthus, a second portion of the liquid suspension is injected into subcutaneous fat lying superior to the malar fat pad region, and a third portion is injected into the reticular dermis proximate to the zygomatic arch area.

Embodiments of this aspect of the technology can include one or more of the following features. In one embodiment of the method the liquid suspension includes equal volume proportions of thawed amnion allograft and saline. In some embodiments, a needle of a syringe containing the liquid suspension is inserted into the facial tissue at a single puncture site and a clinician manipulates a tip of the needle subcutaneously prior to injecting the first portion, second portion, and the third portion. In certain embodiments, the injection of the liquid suspension is in a retrograde motion. And some embodiments feature a 30 minute or less (e.g., 15 minutes, 10 minutes) substantial recovery time from injection. In general, substantial recovery of the human subject means the time needed for the patient to leave a practitioner's office after injection (e.g., after application of ice and pressure).

The methods of the present technology include numerous advantages. For example, as the present technology utilizes amnion allografts, it is believed that the inflammatory response to the injection will be suppressed. Another advantage of the present technology that comes from the utilization of amnion allograft is the antimicrobial properties of the material. Without wishing to be bound by theory, it is believed that there is a decreased risk to infection using such a material. A further advantage of using allogenic amnion materials is that the allogenic cells offers uniformity and quality control as compared to autologous cells and materials. A further advantage of the methods of the present technology is procedure time and recovery time. For example, as the liquid suspension is made and injected within 30 minutes of removing the frozen/cryogenically preserved allograft from a freezer/cooling storage container and recovery time is approximately 10 to 15 minutes, the total time for a clinician from preparing the liquid solution through injection and release of the patient is under 1 hour and preferably under 45 minutes (e.g., 30 minutes, 25 minutes). As defined above, recovery time is the time needed for the patient to leave a practitioner's office after injection (e.g., after application of ice and pressure). Further advantages include a minimal injection time for the method. In general, injection time for the entire face (i.e., both left and right sides) is typically under 10 minutes (preferably within 9 minutes, within 8 minutes, within 6 minutes). These and other advantages will be further described herein.

BRIEF DESCRIPTION OF THE FIGURES

The technology may be more fully understood from the following detailed description taken in conjunction with the accompanying drawings.

FIG. 2, which includes In FIG. 2A a location of an injection site is shown. In FIG. 2B, the location of a patient's malar fat pad is shown. In FIG. 2C, retraction of the needle from the injection site 250 is illustrated.

FIG. 3, which includes FIGS. 3A and 3B provides images of patients post procedure. FIG. 3A shows a patient before and after a conventional PRP rejuvenation procedure, whereas

FIG. 5, which includes FIGS. 5A-5D provides images of a patient before and 12 weeks after a PRP rejuvenation procedure.

FIG. 6, which includes FIGS. 6A-6D provides images of a patient before and 12 weeks after a PRP rejuvenation procedure.

DESCRIPTION

Figure 1:
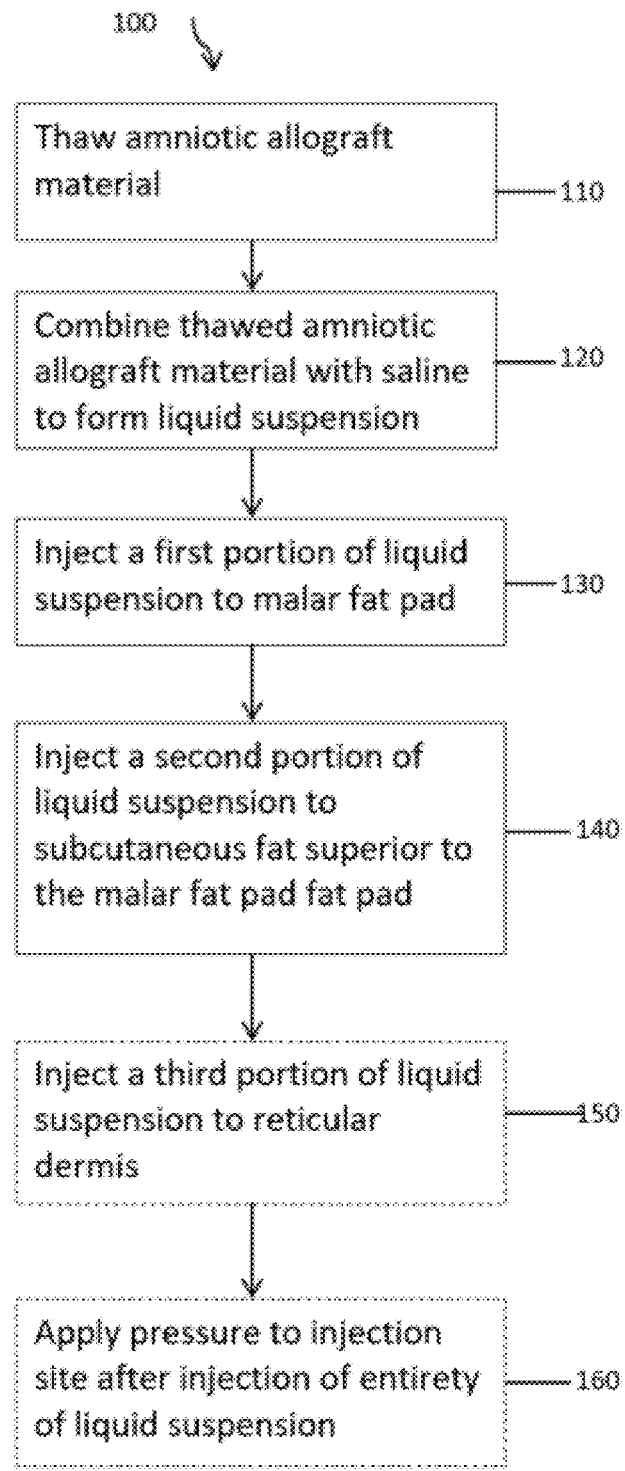
FIG. 1 is a flow chart illustrating a method for augmenting facial tissue in a human subject, according to an embodiment of the present technology.

The technology described herein is directed to the use of amnion allograft to augment volume of the midface. In particular, the methods and processes of the present technology utilize an amnion allograft from a thawed cryopreserved sample originating from the amniotic sac. In embodiments, the cryopreserved amnion allograft (after thawing) is used to form a liquid suspension which includes mesenchymal stem cells. Methods and processes of the present disclosure include injecting a first portion of the liquid suspension into the patient's malar fat pad followed by injecting a second portion into the subcutaneous fat lying superior to the malar fat pad.

In general, the present technology provides numerous advantages over conventional methods for midface rejuvenation. In particular, methods and processes using allogenic cells provide advantages over methods which use constructs that are foreign to the human body. Constructs for volume replacements in the face currently include surgical implants (non-degradable) and injectables, also categorized as dermal filler (degradable). These constructs can provoke a foreign body reaction when implanted or delayed inflammatory reactions months after implantation. The stimulation of giant cells and macrophages of a foreign body produces cytokines that attract fibroblasts. These can lead to granuloma formation in dermal filler injection sites. Fibroblasts can be activated by the transforming growth factor (TGF-β). As mentioned above, the amniotic membrane down regulates the TGF-β and its expression, thus, its use is believed to a reduced risk of foreign body reaction. In addition, it is believed, that the use of allogenic cells, such as amniotic allograft, promotes modulation of the healing of the wound through tissue reconstruction. In general, there is little to no risk of host rejection with an amnion allograft, as it is immunologically inert. See for example, Reference Number 1. Recent research in the area of amnion allograft transplanted into soft tissue of rodents illustrated its use without foreign body reactions, necrosis, or fibrosis. See for example, Reference Number 18.

Another advantage of the methods and processes of the present technology over conventional midface augmentation techniques is application and recovery time. Conventional techniques, even ones that use autologous materials, such as, for example, PRP, require application times of over an hour (due at least in part to harvesting and forming the autologous injectable). In addition, PRP recovery times are longer as bruising occurs more easily and due to the number of injection sites. Another advantage of using allogenic materials over autologous cells includes limiting a risk that the patient, themselves, may lack growth factors needed to inhibit migration of the mesenchymal stem cells to the PRP injection sites.

The present technology utilizes amnion allograft materials. Ethical concerns and the lack of availability of human embryonic stem cells (HESC) make using amniotic epithelial cells (AECs) advantageous. In regards to the tissue formation, there continues to be favorable findings with the use of amnion stem cell to embryonic stem cells for tissue regeneration including results of a 2007 study authored by Ilancheran et al. See for example, Reference Number 7. The study found the clonogenicity, or the ability of a single cell to form a cloned colony and initiate self-renewal, was comparable to that of human embryonic stem cells. The study also showed that AECs did not form teratomas when transplanted in mice, whereas previous studies (e.g., Thomson et al., 1998) showed teratoma formation in immune-deficient mice injected with HESC. See for example, Reference Number 16.

Another advantage of using amnion epithelial stem cells for tissue regeneration is their ability to proliferate without the need for a second cell type as a feeding layer. When cultured, a 2005 study authored by Miki et al. showed the spreading of a feeding layer at the bottom of the culture dish created by the AECs. See for example, Reference Number 12. This is important for the attachment of tissues or "scaffolding" in tissue engineering. The same study showed another advantage to AECs to the large number of the cells yielded from a single amnion, an average over 100 million AECs collected.

FIG. 1 shows a flow chart illustrating a method of the present technology. Method 100 includes four required steps (110, 120, 130, and 140) and two optional steps (150 and 160). Method 100 for augmenting facial tissue of a patient begins with thawing amniotic allograft material as shown in step 110. A previously cryopreserved amniotic allograft will be thawed and utilized. In general, thawing can be accomplished within 30 minutes, and more preferably within 15 minutes (e.g., about 10 minutes, about 9 minutes, about 8 minutes). Once thawed, the allograft material is combined with saline to form a liquid suspension as shown in step 120. In some embodiments, the liquid suspension is formed from equal volumetric amounts of allograft to saline. Once the liquid suspension is formed, it is to be injected into a patient's midface. Without wishing to be bound by theory, it is believed that placement of a cryopreserved amnion allograft of the amniotic suspension into the midface results in improvement of the Ogee curve and the Global Aesthetic Improvement Scale (GAIS) scores comparable to that of PRP. In general, injection is typically conducted within 30 minutes (and preferably 20 minutes, more preferably 15 minutes) of thawing the allograft.

In FIG. 1, method 100 includes two required injection steps (130 and 140) as well as an optional injection step 150. The liquid suspension is placed within a syringe connected to an injection needle, such as a 22-gauge needle. It should be appreciated, that other gauge sizes can be used, such as, for example, 21-gauge or 23-gauge, or any other size the clinician (or physician) selects for use. The syringe is typically graduated such that the liquid suspension can be divided into portions, such as a first portion, a second portion, and in some instances a third portion. In step 130, a first portion, which can be between 0.25 cc and 0.7 cc, and preferably between about 0.35 cc and 0.55 cc, is injected into the malar fat pad through a single injection site. In step 140, a second portion (typically between 0.3 cc and 0.6 cc, and preferably between 0.3 cc and 0.4 cc) is injected into subcutaneous fat superior to the malar fat pad of the patient. In general, there will be a single injection site, and the clinician or physician will inject the first portion followed by the second portion by retracting the tip of the needle from the malar fat pad to the subcutaneous fat superior to the malar fat pad. After injection of the second portion, the clinician or physician can then either retract the needle from the patient's face having delivered the entirety of the liquid solution, or the clinician (or physician) can deliver a third portion of the liquid suspension (a remainder portion) to the reticular dermis, by once again retracting the needle from the subcutaneous fat but not removing the needle from the facial tissue. In general, the clinician (or physician) will deliver the third portion to the reticular dermis proximate to the zygomatic arch area. See for example, step 150 of method 100 shown in FIG. 1. Finally, after the clinician has removed the needle from the patient's facial tissue, pressure and, in some embodiments, ice or other cooling compact is provided as shown in step 160.

To provide additional comfort to the patient, a topical numbing agent can be applied to the facial tissue prior to injection. Typically, a clinician can apply the numbing agent during the formation of the liquid suspension. Prior to injection, the numbing agent should be removed.

In general, to ensure the integrity of the allograft is maintained, injection of the liquid suspension should occur within about 30 minutes of removing frozen allograft from a freezer, or ice or cryogenic storage container. In some embodiments, to further prevent damage or possible injury to the mesenchymal cells in the suspension, the clinician should use care not to inject the liquid suspension too quickly. In embodiments, step 130 will take at least about 35 seconds to inject the first portion of the liquid suspension.

While method 100 shown in FIG. 1 is described as occurring on a single side of the face, it is believed that most patients will desire to augment both the left and right sides of their face. Therefore, the procedures and methods used and shown in FIG. 1 can be repeated and can in some instances occur simultaneously or immediately thereafter. That is, thawing and creation of two liquid suspensions can occur at the same time. The clinician would then use one suspension (a first suspension) on a first side (e.g., left side) followed by using the second suspension on a second side (e.g., right side).

Figure 2A:
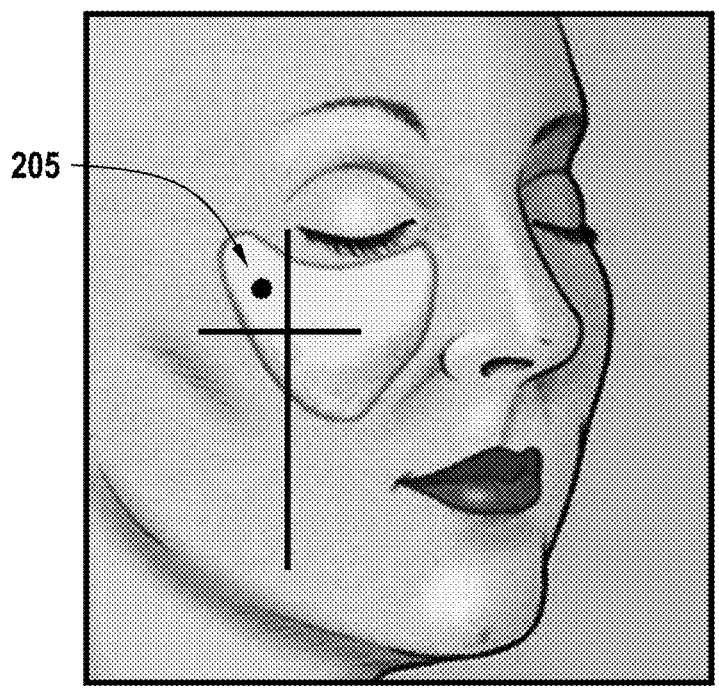
FIGS. 2A, 2B, and 2C, illustrates the location of the injection site.
Figure 2B:
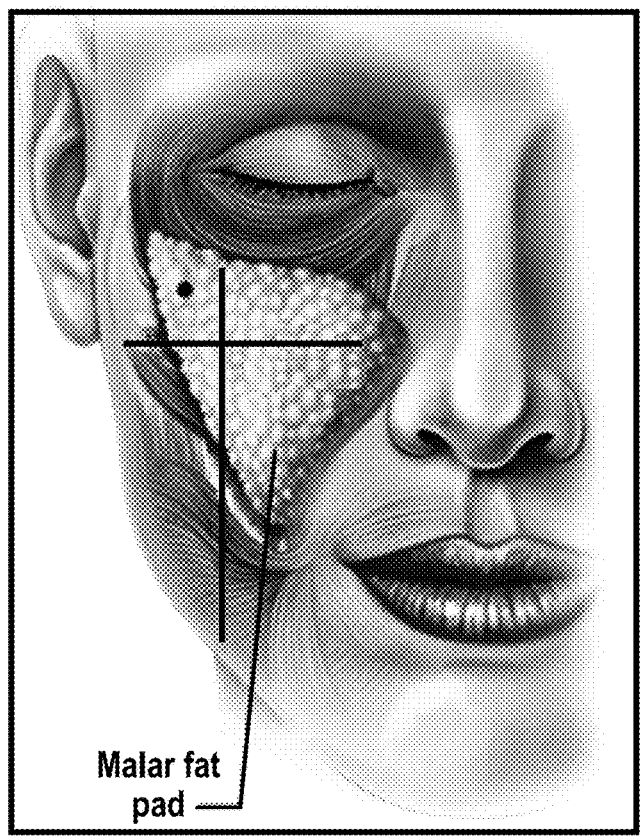
Figure 2C:
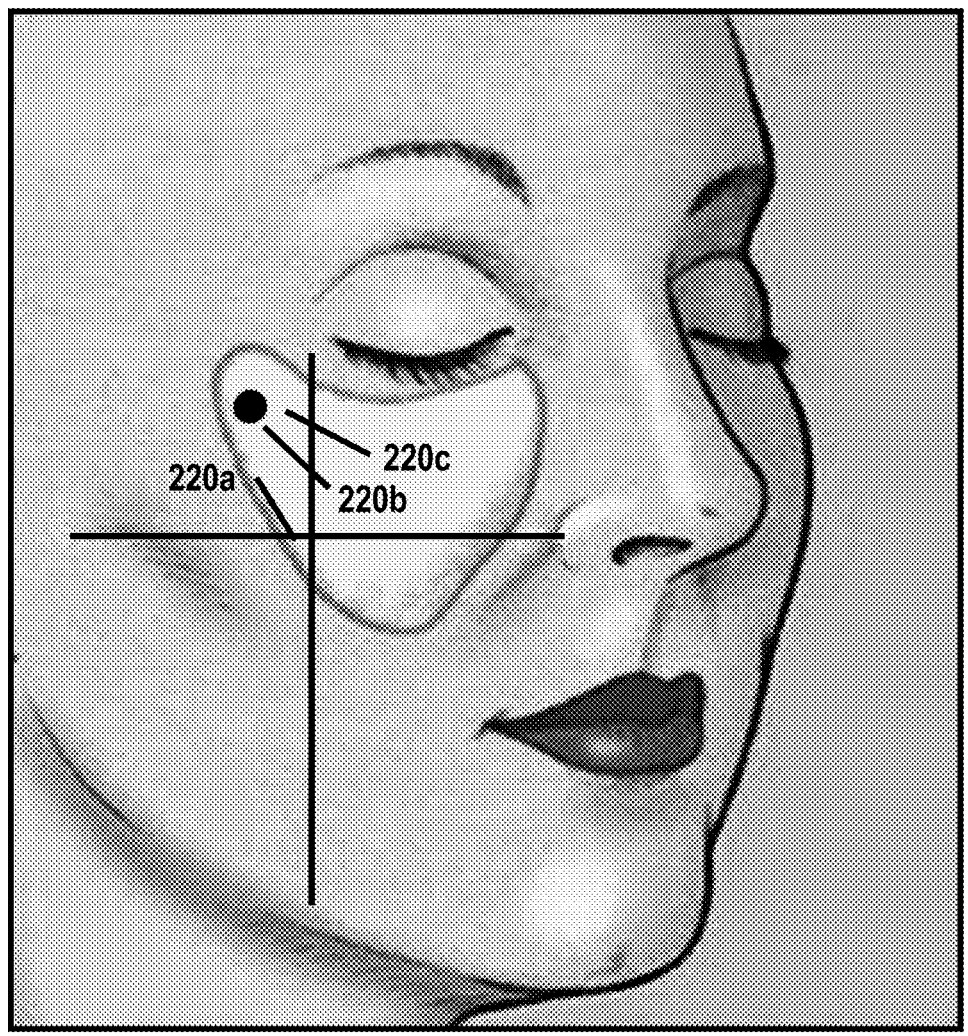

FIG. 2, which includes FIG. 2A, FIG. 2B, and FIG. 2C, illustrates a preferred injection site 205 on a patient's midface. For example, as shown in FIG. 2A, the injection site 205 is typically selected to be on the lateral region (and in particular the superior lateral region) of a patient's underlying malar fat pad. Having identified a preferred location for the injection site, such as the site 205 shown in FIG. 2A, the clinician (or physician) will insert the needle to the depth of the malar fat pad shown in FIG. 2B. Once the clinician (or physician) has reached the malar fat pad, the first portion of the liquid suspension will be injected through the syringe into the needle to reach the malar fat pad. After delivering the first portion, the clinician will retract the needle tip at the site of the injection, as shown in FIG. 2C, and prior to removal from facial tissue, will deliver the second portion and possibly (if desired) the third portion of the liquid suspension. In general, and as shown in FIG. 2C, insertion of the needle should follow the cheek line and at an angle (e.g., see possible injection route 220a on FIG. 2C) to reach the depth of the malar fat pad. To reach the subcutaneous fat superior to the malar fat pad the tip of the needle can be angled upward as shown in possible injection route 220b in FIG. 2C. To reach the reticular dermis, the tip of the needle can once again be angled as shown by possible injection route 220c.

Example 1: Preparation and Injection of Amnion Allograft

Candidacy for midface augmentation using the present technology includes evaluation. Appropriate candidacy is based on chronological age and degree of midface volume loss with assurance of no contraindications. Once candidacy was confirmed the allograft material was obtained and thawed to create the liquid suspension. Thawing can occur just shortly prior to patient's arrival or once the patient has arrived for the procedure. In this example, the allograft was removed from the freezer upon patient's arrival. In general, it will take about ten minutes to thaw the cryopreserved amnion allograft. The allograft was left at room temperature for the full ten minutes. The thawed allograft was then mixed saline in a 1 cc to 1 cc ratio of amnion suspension to injectable saline. The liquid suspension was transferred to syringe (with as minimal manipulation as possible) and capped with a 22 gauge 1" needle. A 1.25" needle can be used if desired and for the reasons described below.

The patient's midface was cleansed thoroughly. To achieve the most desirable aesthetic result, the technique included specific placement of the amnion allograft in the superior lateral region of the malar fat pad in addition to product placement in the subcutaneous fat and reticular dermis of tissue located in the area of the zygomatic arch. The malar fat pad, which lies inferior to subcutaneous fat and the dermis, but superior to the superficial musculoaponeurotic system (SMAS), has minimal structural attachment to it. With intensions of tissue regeneration with amnion injection, too medial placement and tissue growth in the inferior malar fat pad, could potentially exacerbate the nasolabial folds that edge the inferior aspect of the malar fat pad. Tissue growth in superior regions, specifically near the zygomatic arch, suggests potential to appear "lifted" and thus a more desirable aesthetic outcome.

Marking the patient's anatomical landmarks of the face facilitates identification of the proper placement of the initial needle insertion. With chronological age, genetic factors, and environmental factors influencing the degree of the "slippage" of the fat pad on the face, assessment from an educated injector (distinguishing the fatty, fibrous composition of the malar fat pad different than that of overlying subcutaneous fat) via palpation, should also be used along with the anatomical landmarks.

In this example, the lateral border of the malar fat pad was identified by a perpendicular line to the triangular apex of the malar fat pad from the lateral canthus. The superior border of the malar fat pad of the youthful face extends to the orbital rim covering orbicularis oculi muscles. Palpation of the mature face at the most inferior aspect of the orbital rim (mid pupillary line), advancing inferiorly until fatty tissue of the superior border is identified and marked. Zygomatic bone structure peaks at the zygomatic arch which is the most anteriorly projected forward and can be identified from sagittal and axial views.

Insertion of the needle, in this example, was slightly superior and lateral to the zygomatic arch to assure product was placed directly in this region. However, the location of the malar fat pad is individualized and the point of entry can be adjusted to assure placement of product in the lateral superior edge of the malar fat pad with the length of the needle. The 1 inch 22-gauge needle could be changed to a 1.25 inch or a 1.5 inch for distribution of product in a larger area however more "disturbance" occurs to the cells of the allograft with the greater needle length.

Needle insertion followed the cheek line and at an angle to reach the depth of the malar fat pad once inserted to the hub. See, for example line 220a in FIG. 2C. The skin was pinched to avoid hitting periosteum and facilitated the initial placement with patient's exhibiting significant volume loss or thin dermal tissue. With a very slow push, the 0.5 cc of the mixed allograft was injected to the superior lateral tip of the malar fat pad. The speed of injection was slow for minimal disturbance to the allograft, but also can be adjusted for patient comfort. (A burning sensation was reported). Once the liquid suspension was injected into the malar fat pad, the needle was retracted slightly and redirected to a higher plane to inject 0.4 cc of allograft in to the subcutaneous fat lying superior to the malar fat pad. This push occurred slowly and in a retrograde motion placing product adjacent to the zygomatic line stopping just before the needle would retract fully from the skin. The remaining 0.1 cc of product was placed in similar fashion after redirection of the needle into the reticular dermis. (The reticular dermis will show the needle when tented but if the color of the needle can be identified, it is recommended the injector redirect slightly lower to avoid injecting papillary dermis, see for example, line 220c in FIG. 2c). The needle was placed first prior to injecting, after redirection and assurance of proper dermal placement, injection was then retrograde at slow speed until needle was fully retracted from face. All of the liquid suspension in the syringe was injected in its entirety before retracting the needle. Pressure was applied to the insertion point immediately after retraction. Ice was placed for patient comfort then the injection was repeated on the other side of the midface.

Comparison of Amnion Allograft Midface Augmentation to Conventional PRP Midface Augmentation The following description and examples compares conventional PRP (a technique using autologous cells) to the technology of the present disclosure (a technique using allogenic cells).

In orthopedics, the selection of appropriate candidates to undergo a PRP treatment impacts the results. Applying the same principle to the aesthetic patient, chronological age and degree of midface volume loss, would become the largest determinate of candidacy for the study. Candidates were chosen between the age of 40 years to 60 years, consistent data shows substantial malar fat pad degradation in the forties but avoiding having too great of tissue degradation with individuals 60 years of age or more. Too little tissue remaining in the midface could prove challenging when comparing results of PRP to mesenchymal cell placement with an amniotic allograft. Therefore, all candidates were female with an age range of 42 to 58 years. Uniformly the participants refrained from use of non-steroidal anti-inflammatories, aspirin or steroids for 2 weeks prior to the date of procedure. No participants had a history of thrombocytopenia, mast cell activation syndrome, active infection or carcinoma. Additionally, patients with auto-immune disorders were excluded given the lack of conclusive data regarding the origin of cells involved in microchimerism. See for example, Reference Number 20. All participants were non-smokers. Post procedure all refrained from undergoing any cosmetic procedures altering the dermis or tissue of the midface. SPF protection was used on the face along with minimal sun exposure, to lessen damage caused by photoheat.

The Harvest Smartprep system, a part of Harvest Technologies through Terumbo BCT (Lakewood, Colo.), was utilized in the PRP collection having shown advantages to competitors for platelet concentration and efficiency of platelet capture. See for example, Reference Number 9. For the amnion allograft, Organogenesis ReNu® advanced amniotic allograft (commercially available from Organogenesis, Inc., Canton Mass.) was chosen as an established FDA regulated company with HCTP 361 registered product. The allograft includes all growth factors and extracellular matrix components of the amniotic fluid in addition to containing cryopreserved mesenchymal cells. Additionally, the Organogenesis ReNu® advanced amniotic allograft is well published in orthopedic uses, both in surgical and non-surgical in-office settings, without record of adverse event. See for example, Reference Number 17.

Example 2: ReNu® Advanced Amnion Allograft

The amnion allograft (ReNu® allograft commercially available from Organogenesis, Canton, Mass.) was delivered onsite to the surgical office and kept in a cryogenic state prior to patient injection. Once removed from ice, the allograft was mixed, 1 cc of injectable saline to 1 cc of allograft, as established protocol with its use in orthopedics. The allograft was allowed to thaw for 5-10 minutes and carefully placed in a 3 cc syringe for injection within 30 minutes of its removal from ice.

Figure 3A:
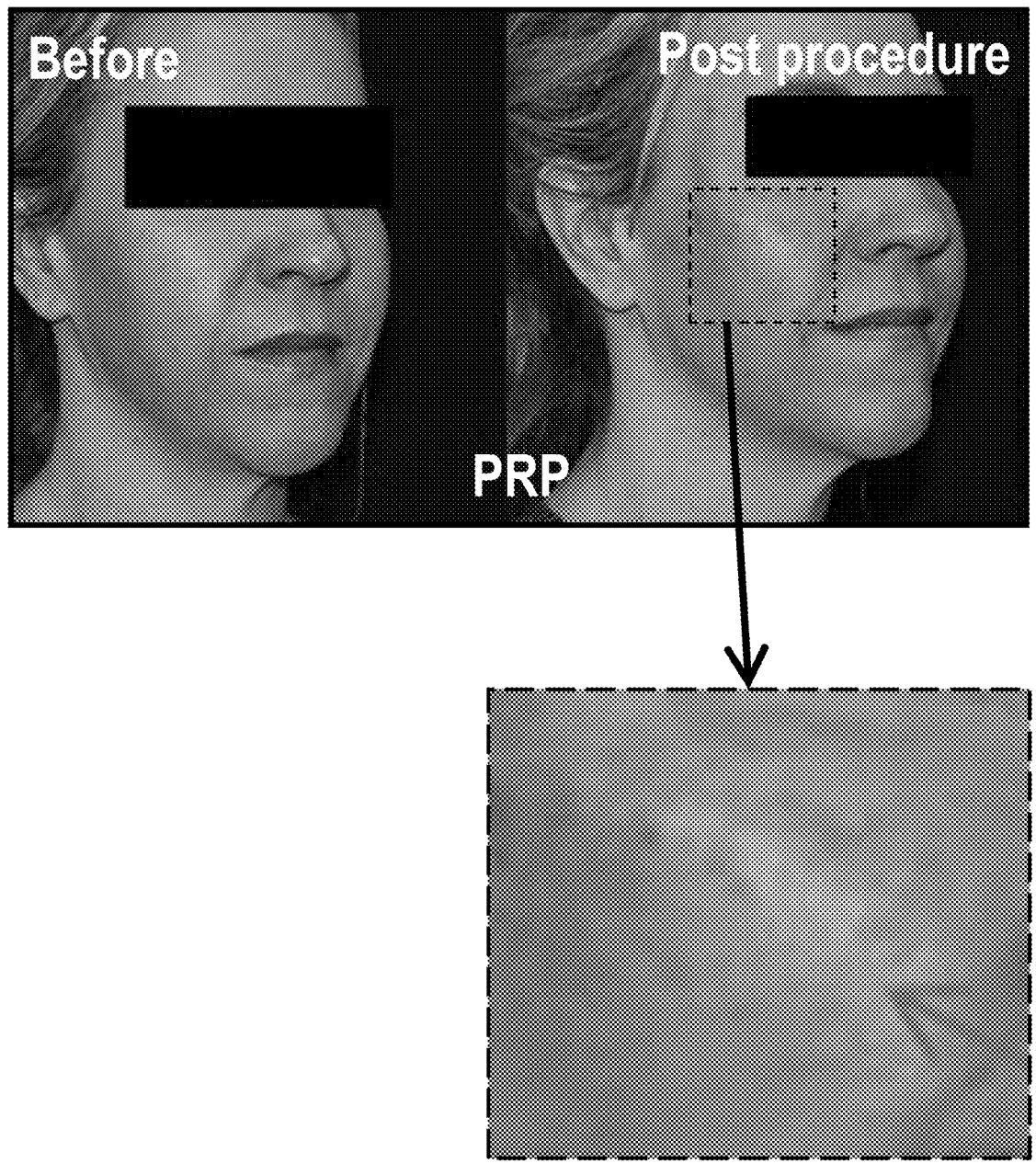
Figure 3B:
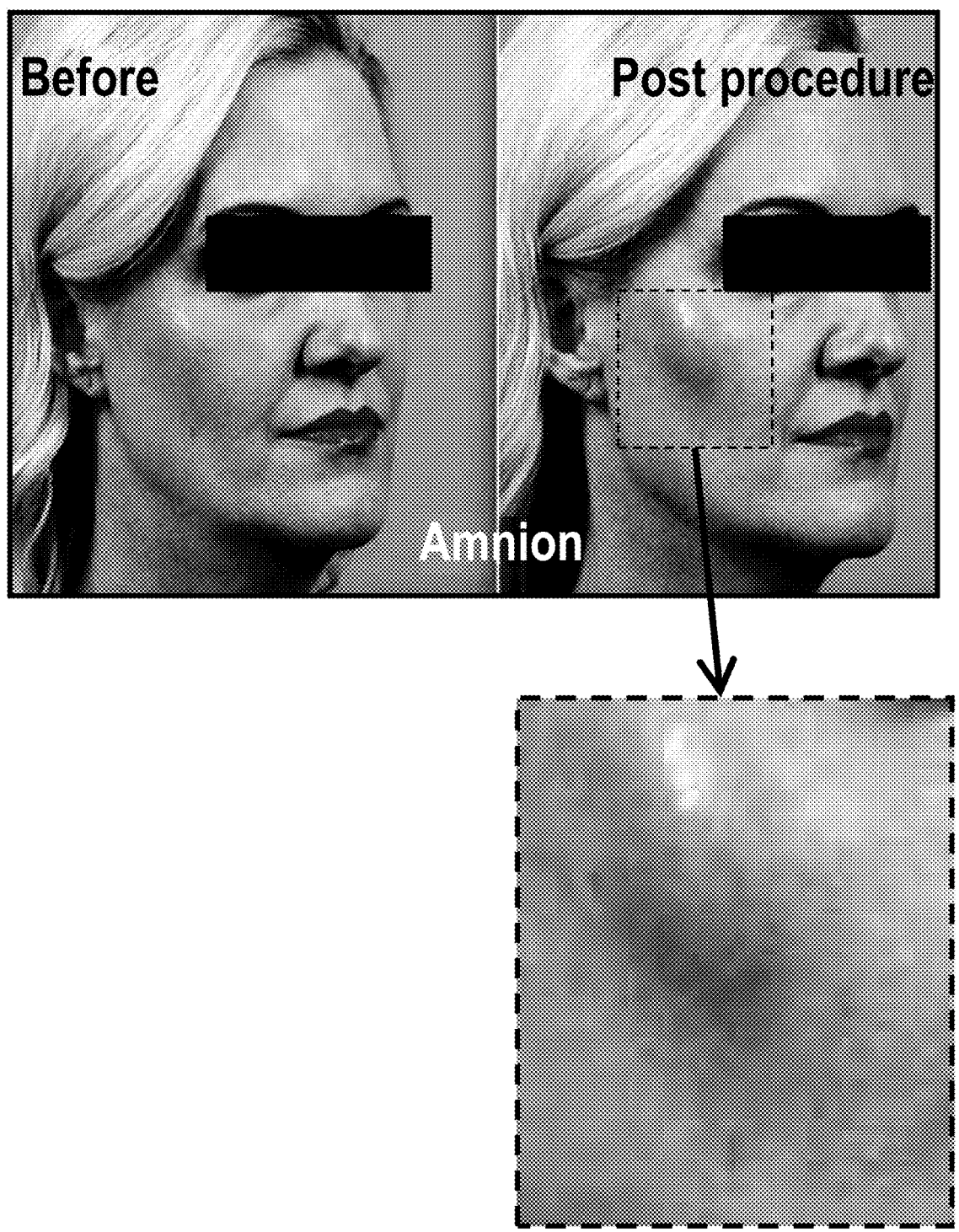
FIG. 3B shows a patient before and after a rejuvenation procedure in accordance with the present technology.

Topical numbing was placed in the medial to lateral region of the patient's midface to minimize discomfort, using a 22-gauge needle per Organogenesis recommendation for allograft delivery; however, per Organogenesis recommendation, no lidocaine was applied to the allograft itself. The viscosity of the amnion allograft was slightly higher than that of PRP, although slow delivery of product is desired for both patient comfort and to minimize disruption of the amnion allograft. After 10 minutes, the numbing agent was removed and the area cleansed with alcohol and chlorhexidine. A single puncture was made in the medial to lateral malar fat pad region adjacent to the lateral canthus. The allograft was injected slowly in to tissue, first below the reticular dermis and, upon readjustment of needle placement, the subcutaneous fat. Product was distributed throughout the length of the one-inch needle for a total of 1 cc per side. Ice packs were placed for patient comfort after pressure was applied forcoagulation of puncture wound. Post procedure pictures were taken within 20 minutes of injections and are shown in FIG. 3B. Additional photos were taken at regular intervals (e.g., 1 week, 2 weeks, 4 weeks, 8 weeks, and 12 weeks) thereafter. See for example, FIGS. 6A-6D, showing a patient before injection and at 12 weeks thereafter.

Example 3: Platelet Rich Plasma Treatment

The Harvest Smartprep system (30 cc kits) were used with established procedure prep of PRP collection performed uniformly. A total of 30 cc of blood was drawn from the patient's antecubital area and placed in the chamber for centrifuge. A numbing agent was topically applied to injection sites and removed after 15 minutes. Injection sites were thoroughly cleansed. After centrifuge was complete, the platelet poor plasma was removed, the buffy coat identified and the platelet rich plasma drawn into a 10 cc syringe. A sodium bicarb and 2% lidocaine mixture (0.1 cc/0.4 cc respectively) was added to the PRP, followed by 0.25 cc of calcium chloride mixed through a female to female connector. The PRP solution was placed in two 3 cc syringes secured by a 27-gauge needle. The four participants yielded between 4-5 cc of PRP each. For the study comparison purpose and uniform assessment of the midface, 1 cc of PRP was injected to the same lateral mid face region, both reticular dermis and subcutaneous placement, as performed with the ReNu® amnion allograft. Remaining PRP was placed in other regions requested by patient including temples, upper lip and tissue of the neck. Massage was performed to the PRP once placed. Post procedure pictures were taken and are shown in FIGS. 3A and 5A-5D.

Discussion Comparing Example 2 and Example 3

Given the nature of aesthetics, it was determined the effectiveness of the injections are best assessed by pictures for comparison at baseline, immediately post procedure, one week, 4 weeks, 8 weeks and 12 weeks post procedure. A 12 week study was chosen for full assessment of both the amnion allograft and PRP treatment, allowing for maximal achieved results. Pictures showed the improvement in tissue volume of the midface from baseline as well as the timing of the changes.

Immediate post procedure pictures show that the ReNu® injected candidates have little to no change in appearance with exception of mild edema in the injection area. PRP candidates show discoloration of injected areas in addition to edema. See, for example, FIG. 3B and compare to FIG. 3A.

Oblique and side views of the study participants allow for clear assessment of the Ogee curve of the midface. The improvement of the skin coloration and texture can be observed in frontal views as well as improvement in nasolabial folds, marionette lines, and tear troughs. This was seen with both procedures comparatively, with more pronounced differences for the candidates in their forties.

The changes in midface appear more distinguished with ReNu® amnion injections versus PRP at 4 weeks post procedure. The changes in all candidates include some improvement in the Ogee curve specifically assessed upon oblique and side views. A deduction could be made that the Ogee curve improvement are more timely with the amnion than the results of the platelet rich plasma. Results at 12 weeks post of the amnion allograft in comparison show efficacy to those of PRP. Compare for example FIGS. 5A-5D to FIGS. 6A-6D.

Assessing the Midface of the Aging Patient

A typical way to assess aging and improvement after an augmentation procedure is to assess a patient's Nasolabial folds. The Nasolabial folds are visible folds extending between the base of the nose and the outer lip area. The degree of shallowness of the Nasolabial folds to a more pronounced indentation indicates aging of the midface. From oblique angles, the Ogee curve can be assessed by drawing angles along the cheek lines intercepting to assess the degree of the curve and its location superior or inferior on the face.

Figure 4:
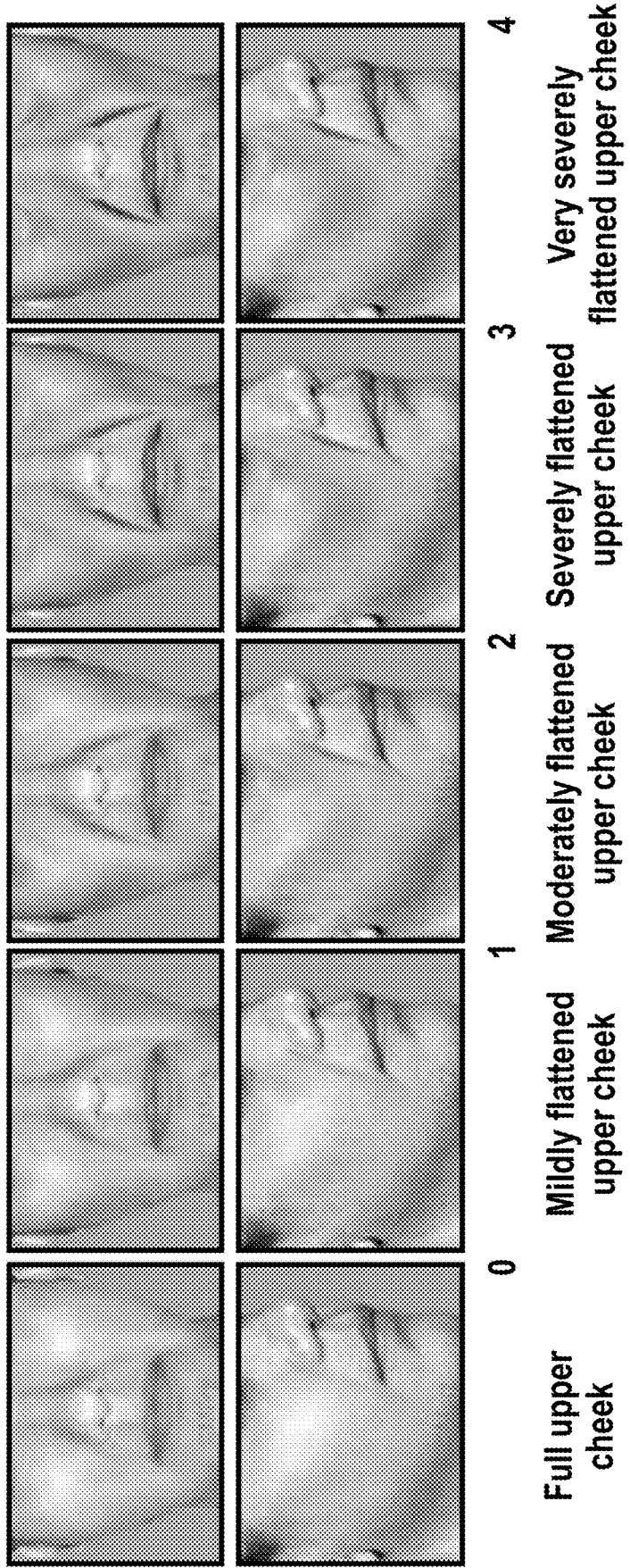
FIG. 4 provides a scale for use in assessing midface aging.
Figure 5A:
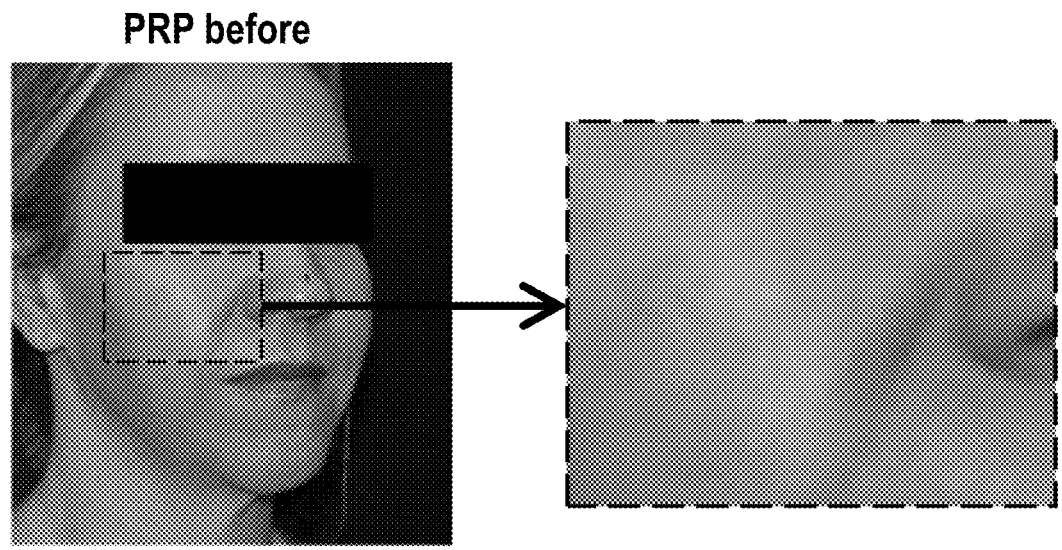
FIGS. 5A and 5B show the patient prior to the procedure and FIGS. 5C and 5D show the patient 12 weeks after.
Figure 5C:
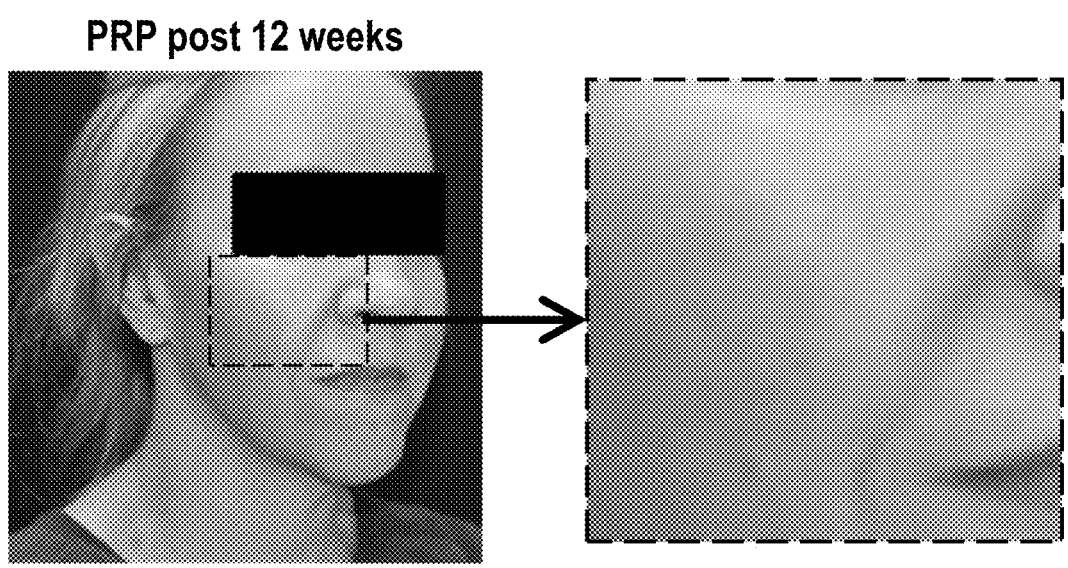
Figure 5B:
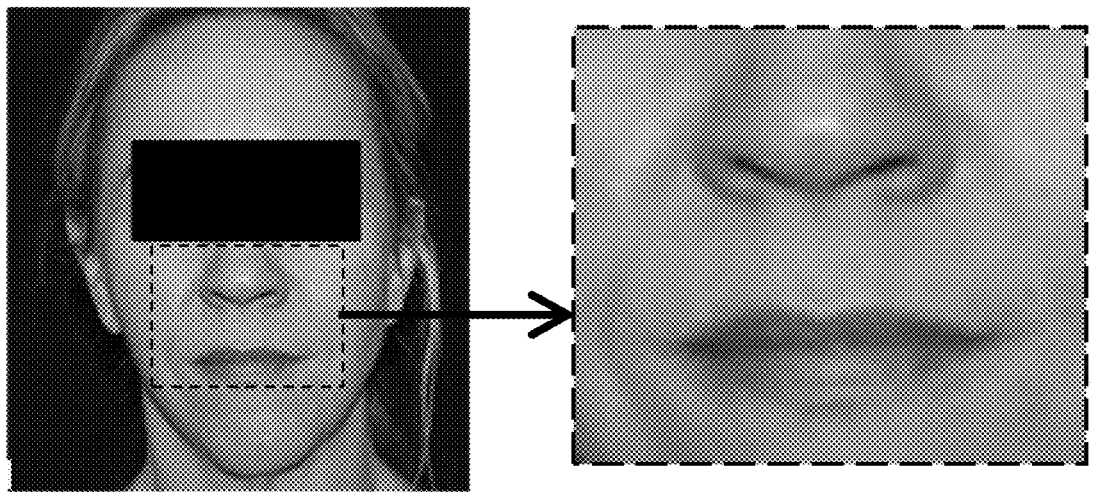
Figure 5D:
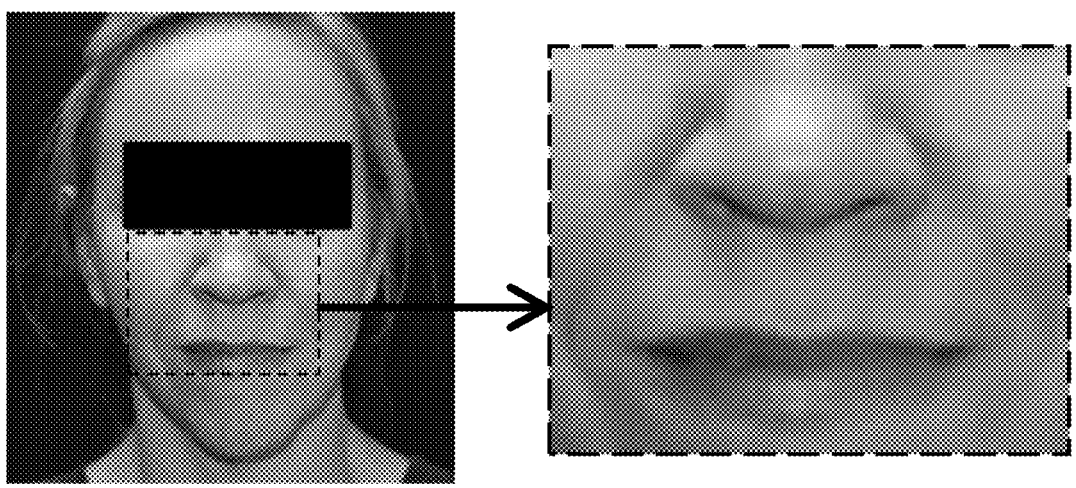
Figure 6A:
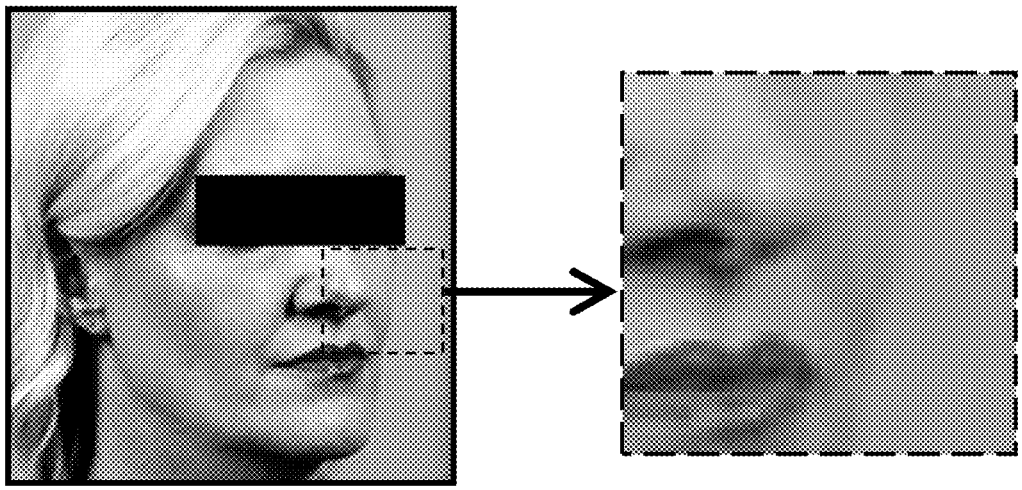
FIGS. 6A and 6B show the patient prior to the procedure and FIGS. 6C and 6D show the patient 12 weeks after.
Figure 6C:
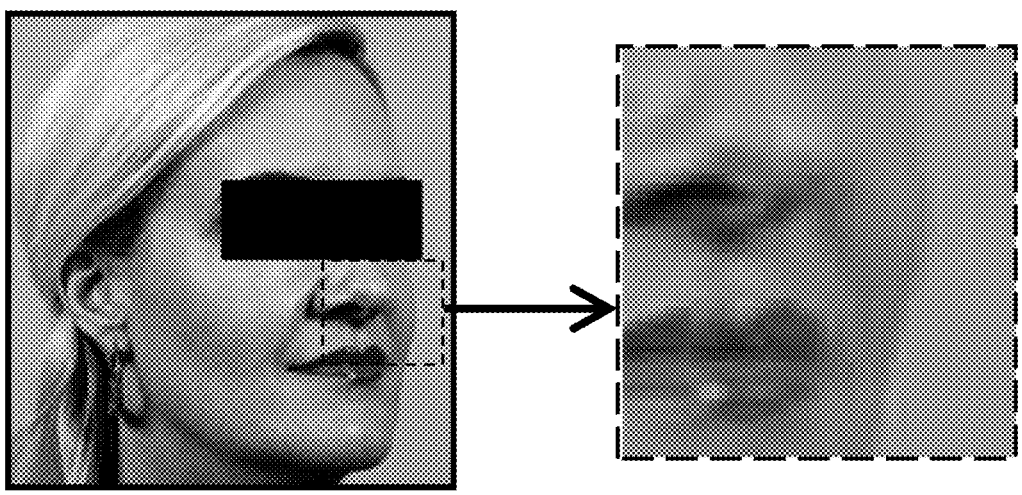
Figure 6B:
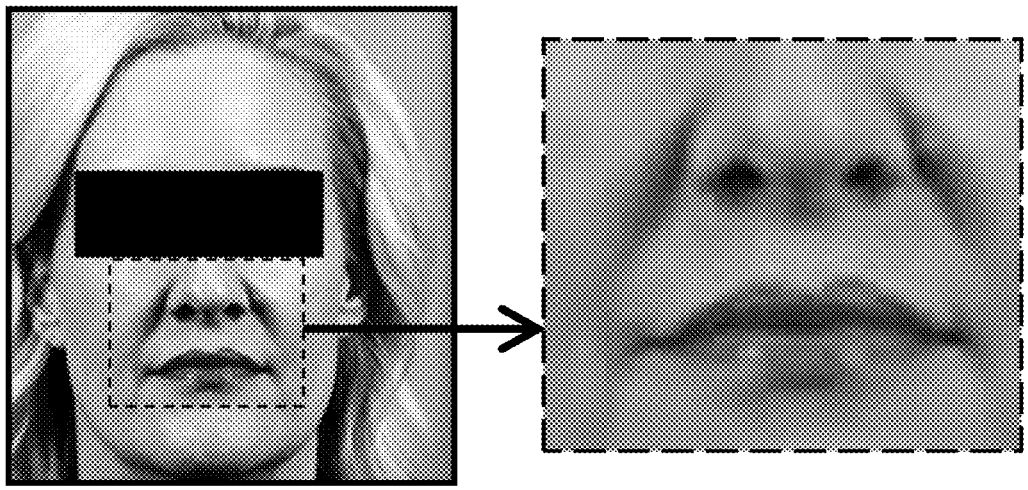
Figure 6D:
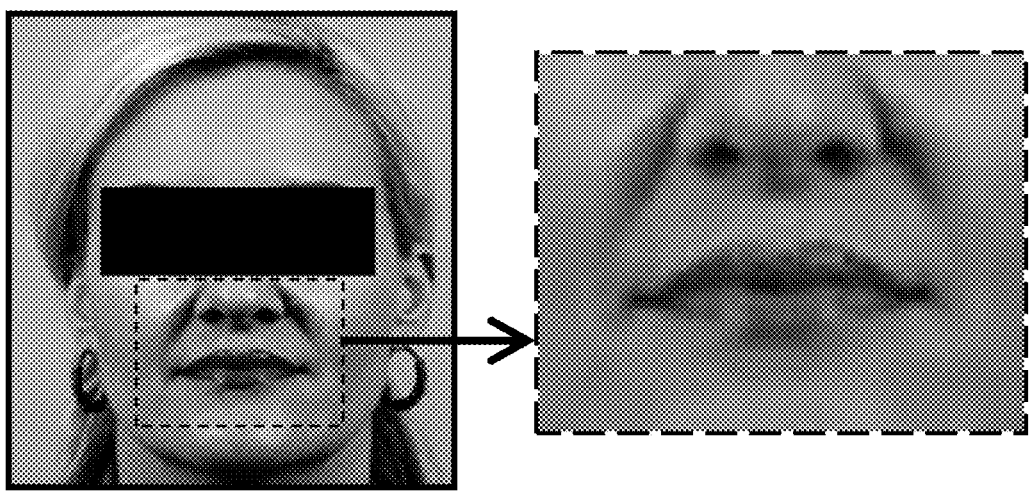

Referring to FIG. 4, a scale of 0 to 4 for the assessment of aging is provided. The lowest number on the scale, 0, indicates a shallow fold with a visible Ogee curve minimally displaced inferiorly. The highest number on the scale is given a value of 4, which represents pronounced indentation of the Nasolabial folds with flattening of the Ogee curve.

The efficacy of the amnion results compared to those of PRP at 12 weeks was assessed visually, with the former having a superior result (e.g., a visibly noticeable result). The evaluation of the amnion group as superior could result in part from the visual assessment of the patients in person by the researchers. To quantify results, a facial grading scale was used with an assigned baseline and post procedure scoring of midface volume loss as described on Table I. From oblique angles, the Ogee curve can be assessed by drawing curves along the cheek lines that intercept to assess the degree of the curve and its location as superior on the face. A decrease in score after the procedure is indicative of improvement.

TABLE I

Facial Grading Scale Used to Determine the Degree of Volume Loss at Baseline and the Improvement or Lack Thereof Post Treatment.

| Participant (#) | Age (Years) | Treatment received | Initial midface volume loss: facial scale | 12 weeks post-treatment volume loss: facial scale |
|---|---|---|---|---|
| 1 | 43 | PRP | 2 | 1 |
| 2 | 47 | Amnion | 3 | 2 |
| 3 | 46 | PRP | 3 | 2 |
| 4 | 42 | Amnion | 2 | 1 |
| 5 | 44 | PRP | 3 | 2 |
| 6 | 58 | Amnion | 4 | 3 |
| 7 | 58 | PRP | 3 | 3 |
| 8 | 49 | Amnion | 3 | 2 |

Referring to FIG. 5, the PRP patient at baseline could be described as a 2 with flattening of the Ogee curve and more pronounced nasolabial folds to a moderate degree. Following treatment, the curve of the cheek improved as well as the lines of the midface to a 1 or more mild degree of visible aging.

Referring to FIG. 6, the Amnion patient at baseline exhibited more severe flattening of the cheek with inferior displacement of volume contributing to more pronounced nasolabial folds classified as a 3. Post treatment picture shows improvement to a 2.

Example 4: ReNu® Advanced Amnion Allograft Patients

The retrospective study included 4 patients who underwent amnion allograft implantation of the midface region. The patients were all female between 42-58 years of age showing signs of midface volume loss including flattening and inferior placement of the Ogee curve and pronounced nasolabial folds. Similar requirements were imposed for this group of patients as before: no NSAID use for two weeks prior to study, no active infections, no autoimmune disorders, no prior cosmetic procedures to alter the midface section for 12 weeks prior to injection. Additionally, patients were non-smokers, and all were required to avoid NSAIDs for 2 weeks post procedure. Written charts and photo data was stored in a secure database in the private clinic.

Similarly to Example 2, Organogenesis ReNu® amnion allograft was chosen. The product is a HCTP-361 registered product of an established FDA regulated company with a clean safety profile and well published data for use in human soft tissues and joints, both in the perioperative setting and in-office, mainly of the orthopedic discipline. The primary investigator performed the procedures to avoid bias of variance of technique.

Procedure

The procedure followed for this example was identical to that discussed in Example 2. Injections were completed within 90 seconds. Patient feedback was collected during and immediately following procedure. Follow up communication occurred 24 and 48 hours post injection and at 4 and 8 weeks post injection.

Results

Photographic data was determined to be the best assessment of improvement with the facial grading scale number assigning a quantitative value. Pre and post procedure scores were compared, and the results compiled in Table II using the same facial grading scale presented in FIG. 4.

TABLE II

Facial Grading Scale Used to Determine the Degree of Volume Loss at Baseline and the Improvement or Lack Thereof Post Treatment.

| Participant (#) | Age (years) | Initial midface volume loss: facial scale | 12 week post-procedure midface volume loss: facial scale |
|---|---|---|---|
| 1 | 42 | 2 | 1 |
| 2 | 58 | 4 | 3 |
| 3 | 58 | 3 | 2 |
| 4 | 49 | 2 | 2 |

Figure 7:
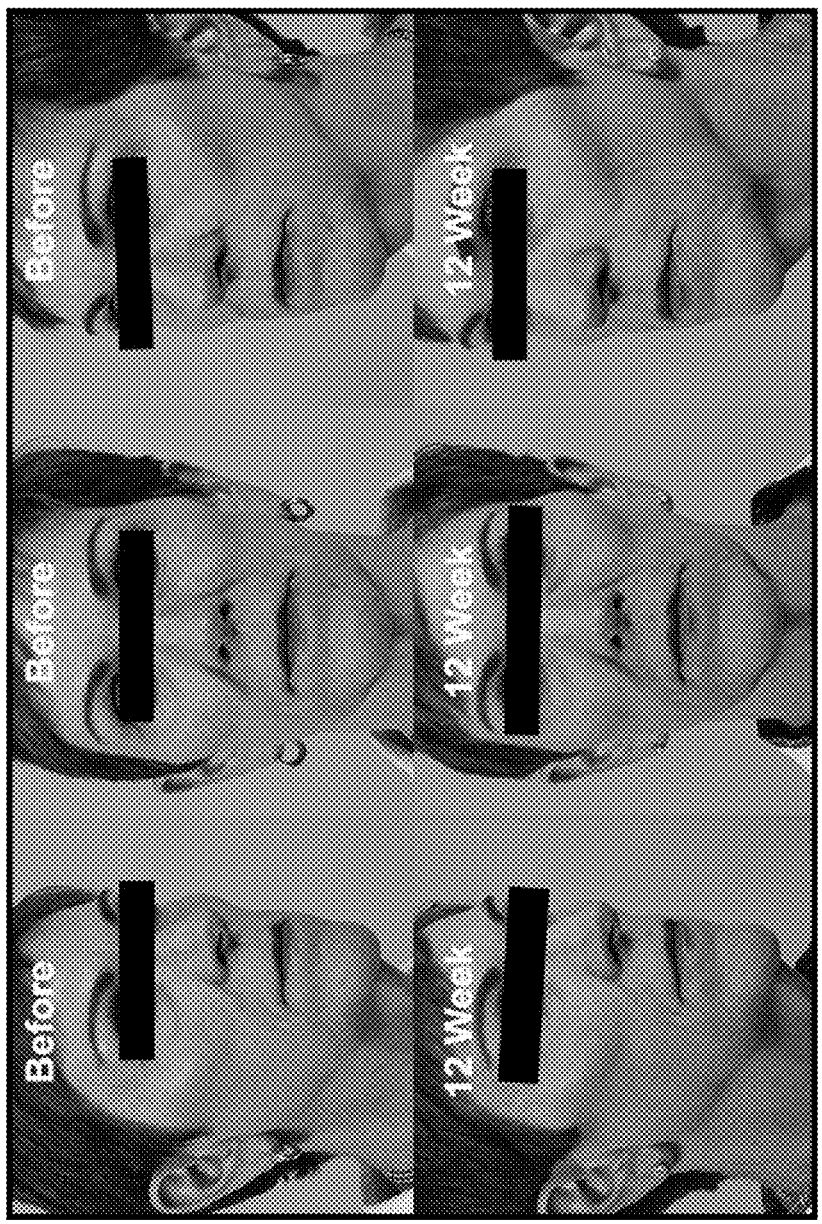
FIG. 7 provides an image of a patient before and after 12 weeks after an amnion allograft procedure.

The oblique views illustrated improvement to the Ogee curve most predominantly. Pictures before and 12 weeks after the procedure for a representative participant (for example, participant no. 3) is provided as FIG. 7. As seen in FIG. 7, there is a noticeable increase in volume in the area above to the patient's malar fat pad. Subtle improvements were noted in all patients with frontal and oblique views illustrated. Frontal views showed improvement of the nasolabial folds in addition to skin coloration and texture.

Discussion

As done in previous examples, patient feedback was collected prior to, during, and following the procedure using a series of questions to assess experience and perspective. Specifically, discomfort level and side effects were assessed during and immediately post procedure. A pain scale of 1-10 (1 being minimal discomfort and 10 representing extremely painful) was used to quantify. Two participants reported a 4 on the pain scale and the other two participants reported a 3. All discomfort subsided within seconds of retracting the needle from the face. The sensation was described using four descriptions including; achy, sharp, tolerable stinging, and pressure. Minutes following the injections, a small raised area was noted where allograft was placed. Each participant stated they felt no discomfort and described feeling "normal." This suggests an aesthetic alternative treatment for patients seeking a natural appearing outcome with limited procedure and down time in addition to minimal discomfort.

One patient (#4) did not show significant enough improvement to change the scale grade assigned before and after procedure. Some change was noted, but increase in facial volume due to weight gain post injection, skewed the visual comparison. This presented a variable that could not isolate the amniotic allograft as sole reason for modification.

Participant Perspective

Patients were also assessed for discomfort level during and post procedure, along with side effects from the procedure. Recipients of the amnion allograft described a burning sensation upon injection that was decreased upon completion of the injection (<3 minutes) and the immediate application of ice to the site. The pain scale ranged from 2-7 on a scale of 10 per participant report during the injection. One participant described the feeling of tenderness, "like a bruise," in the cheek. All four participants reported all discomfort subsided prior to leaving the clinic site within 20 minutes post procedure. Next day follow up reported 2 of 4 participants with small hematomas at the large bore needle injection site; however, unilaterally. One participant had remaining edema that was more evident on one side. This subsided three days post injection. No discomfort was reported in follow up, 1 and 3 days post treatment.

Participants receiving platelet rich plasma treatment reported a mild burning sensation upon injection with no greater than a 4 on a pain scale of 10. Part of the discomfort was reported during massage of the PRP rather than injection itself. Use of lidocaine mixed with PRP, as well as smaller needle size, could attribute to less discomfort with injection when compared to the amnion stem injections. The use of lidocaine with the amnion allograft is not recommended, but study showed no negative impact on the effectiveness of the PRP when used with anesthetic. One-day post procedure, all four participants showed remaining edema in the mid face region. Hematomas were present in 3 of the 4 injected with PRP, with 1 recipient experiencing significant amount on one side. As PRP contains hematocrit, it is unclear to what extent the hematomas were the appearance of the unabsorbed PRP below the skin versus trauma from the puncture and needle advancement. Tenderness remained with patients for several days. Edema resolved after 3 days in 1 patient, 4 days in 2 patients and the patient showing significant hematoma reported that edema subsided after 1 week.

Provider Prospective

The time and preparation for the two different procedures (PRP vs. amnion allograft) varied greatly. The amnion allografts require no blood collection or wait time in a centrifuge. There is an approximate 10-minute duration to allow the allograft to thaw after removal from ice and injecting the saline to the solution. There is ease in the packaging and multiple labels for tissue logs and documentation. The injection time from initial puncture to needle withdrawal was less than 120 seconds per side. Five to ten minutes were spent with each patient post injection, applying pressure, ice, gentle massage and conversing with the patient about what they were experiencing. It is reasonable to allot 30 minutes for the injection in office with minimal prep required by the injector.

In contrast, the PRP injection procedure requires 1 hour from start to finish if done as mono therapy. Use of PRP in aesthetics however is generally paired with microneedling or injection of hyaluronic acid filler to obtain optimal results. This will increase the amount of injection time. Preparation time for PRP is more extensive and it varies pending the system used for collection. Overall, more is required in both time and preparation for PRP treatment when compared to the ReNu® advanced allograft injection.

CONCLUSION

Results established efficacy of aesthetic improvement in midface volume with amnion allograft when compared to aesthetic improvement using platelet rich plasma. The ease of the in-office procedure, minimal downtime, reports of no adverse effects based on large amounts of data of its use in human soft tissues and joints, and expedited results, advocate its place in aesthetics. Serving as an alternative for patients that are poor candidates for PRP, the injections with ReNu® advanced amnion allografts will allow an option for patients weary of surgical enhancement and/or dermal filler injections. Platelet rich plasma therapy for aesthetic purposes is used alongside hyaluronic acid derived fillers. Given the hyaluronic acid naturally found in amniotic epithelial stem cells, it is envisioned that amniotic allografts and hyaluronic acid derived fillers can be used in a combined therapy. In theory, the immunoprivileged nature of the amnion stem cells could decrease the potential of delayed foreign body reaction to dermal filler when performed in conjunction. Allowing the individuals genetic code to guide tissue regeneration assures the "natural look" of the anti-aging benefits for amnion stem cell injections.

REFERENCES

Each of the foregoing references, which are identified by a reference number (e.g., 1, 2, . . . ) are incorporated herein by reference.

1. Anderson J J, Adeleke A T, Rice B Swayzee Z (2017) Surgical treatment of peroneus brevis tendon repair with and without human amniotic allograft: a comparison study. Clinical Surgery 2: 1515.
2. Bitterman-Deutsch O, Kogan L, Nasser F (2016) Delayed immune mediated adverse effects to hyaluronic acid fillers: report of five cases and review of the literature. Dermatology Reports 7(1): 5851.
3. Carruthers A, Carruthers J (2010) A validated facial grading scale: The future of facial ageing measurement tools, Journal of Cosmetic and Laser Therapy, 12(5): 235-241.
4. Friel N A, de Girolamo L, Gomoll A H, Mowry K C, Vines J B, Farr J (2016) Amniotic fluid, cells, and membrane application. Operative Techniques in Sports Medicine 25: 20-24.
5. Gassner H G, Rafil A, Young A, et al (2008) Surgical Anatomy of the Face Implications for Modern Facelift Techniques. Arch Facial Plastic Surgery 10 (1): 9-19.
6. Horn D B, Linzie B M, Huang T C (2007) The healing effects of autologous platelet gel on acute human skin wounds. Arch Facial Plastic Surgery 9 (3): 174-183.
7. Ilancheran S, Michalska A, Peh G, Wallace E M, Pera M, Manuelpillai U (2007) Stem cells derived from human fetal membranes display multilineage differentiation potential. Biology Reproduction 77: 577-588.
8. Kaer M, Garg R K, Singla S (2013) Analysis of facial soft tissue changes with aging and their effects on facial morphology: A forensic perspective. Egyptian Journal of Forensics 5(2): 46-56.
9. Kevy S V, Jacobson M S (2004) Comparison of Methods for point of care preparation of autologous platelet gel. Journal of Extracorporeal Technology 36(1): 28-35.

10. Kim I, Bang S I, Lee S K, Park S Y, Kim M, Ha H (2014) Clinical application of allogenic implantation of adipogenic differentiated adipose-derived stem cells. Stem Cells Transitional Medicine 3(11): 1312-1321.
11. Knight M A, Evans G R (2004) Tissue engineering: progress and challenges. Plastic Reconstructive Surgery 114: 26E-37E.
12. Mild T, Lehmann T, Cal H, Stolz D B, Strom S C (2005) Stem cell characteristics of amniotic epithelial cells. Stem Cells 23: 1549-1559.
13. Niknejad H, Peirovi H, Jorjani M, Ahmadiani A, Ghanavi J, Seifalian A M (2008) Properties of the amniotic membrane for the potential use in tissue engineering. European Cells and Materials 15: 88-99.
14. Selafani A P, Romo T R III, Ukrainsky G, et al (2005) Modulation of immune response and soft tissue in growth in synthetic and allogenic implants with platelet concentrate. Arch Facial Plastic Surgery 7(3): 163-169.
15. Shimberg M (1938) The use of amniotic fluid concentrate in orthopaedic conditions. Bone Joint Surgery 20: 167-177.
16. Thompson J A, Itskovitz-Eldor J, Shapiro S S. Waknitz M A, Swiergiel J J, Marshall V S, Jones J M (1998) Embryonic stem cell lines derived from human blastocysts. Science 282: 1145-1147.
17. Vines, J B, Aliprantis A O, Gomoll A H, Farr J (2015) Cryopreserved amniotic suspension for the treatment of knee oseteoarthritis The Journal of Knee Surgery 29 (6): 443-450.
18. Buday, M C, Ozturk, M (2019) Evaluation of folded amniotic membrane and injectable amniotic membrane pieces as soft tissues filler materials. Auris Nasus Larynx 46(3): 451-456, (epub Oct. 30 2018)
19. Nu Tech Medical (2012) NuCel: product overview Vol 1: 1-2.
20. DiGermino, C, Bernier M, deCabo R, Barbani B (2016) Amniotic epithelial cells: A new tool to combat aging and age-related diseases? Fron Cell Dev Biol 4: 135.
21. Werber B, Martin E (2013) A prospective study of 20 foot and ankle wounds treated with cryopreserved amniotic membrane and fluid allograft. Jour of Foot and Ank Surg 52 (5): 615-621.

What is claimed is:

1. A method of augmenting facial tissue in a human subject using a thawed liquid suspension comprising cryopreserved amnion allograft comprising amniotic membrane and amniotic fluid cells, the method comprising injecting a first portion of the thawed liquid suspension into a malar fat pad of the human subject followed by injecting a second portion the thawed liquid suspension into the subcutaneous fat lying superior to the malar fat pad.

2. The method according to claim 1, wherein the thawed liquid suspension is formed by thawing cryopreserved amnion allograft and mixing equal portions of thawed cryopreserved amnion allograft and saline.

3. The method according to claim 2, wherein the thawed liquid suspension is formed and injected within 30 minutes of removing frozen cryopreserved amnion allograft material from a freezer, ice or cryogenic storage container.

4. The method according to claim 1, wherein the first portion of the thawed liquid suspension is injected into the superior lateral region of the malar fat pad.

5. The method according to claim 1 further comprising injecting a third portion of the thawed liquid suspension into reticular dermis proximate to the zygomatic arch area.

6. The method according to claim 5, wherein the first portion of the thawed liquid suspension has a volume of 0.5 cc, the second portion of the thawed liquid suspension has a volume of 0.4 cc, and the third portion of the thawed liquid suspension has a volume of 0.1 cc.

7. The method according to claim 1, wherein a 21 to 23 gauge needle is used for the injections.

8. The method according to claim 1, wherein the liquid suspension is stored in a barrel capped with an injection needle and the entirety of the liquid suspension is injected prior to retracting the injection needle from the facial tissue of the human subject.

9. The method according to claim 8, further comprising applying pressure to an injection site immediately after retracting the needle from the facial tissue.

10. The method according to claim 8, wherein total injection time is under four minutes.

11. The method according to claim 1, wherein the first portion of the thawed liquid suspension has a volume of 0.5 cc and the second portion of the thawed liquid suspension has a volume of 0.4 cc.

12. The method according to claim 1, wherein the first portion of the thawed liquid suspension is injected slowly to prevent disturbance of the cells in the amnion allograft.

13. The method according to claim 1, further comprising applying and removing a topical numbing agent to the facial tissue of the human subject prior to injecting the thawed liquid suspension.

14. The method according to claim 1, wherein the thawed liquid suspension is injected in an in-office procedure under 1 hour.

15. The method according to claim 14, wherein the liquid suspension is injected in an in-office procedure with substantial recovery of the human subject within 1 hour.

16. A method of augmenting facial tissue in a human subject, the method comprising: forming a liquid suspension including thawing frozen amnion allograft comprising amniotic membrane and amniotic fluid cells for no more than 10 minutes and mixing the thawed amnion allograft with saline; injecting the liquid suspension within 20 minutes of thawing the frozen amnion allograft, wherein a first portion of the liquid suspension is injected into medial to lateral malar fat pad region adjacent to the lateral canthus, a second portion of the liquid suspension is injected into subcutaneous fat lying superior to the malar fat pad region, and a third portion is injected into the reticular dermis proximate to the zygomatic arch area.

17. The method according to claim 16, wherein the liquid suspension includes equal volume proportions of thawed amnion allograft and saline.

18. The method according to claim 16, wherein a needle of a syringe containing the liquid suspension is inserted into the facial tissue at a single puncture site and a clinician manipulates a tip of the needle subcutaneously prior to injecting the first portion, second portion, and the third portion.

19. The method according to claim 18, wherein injection of the liquid suspension is in a retrograde motion.

20. The method according to claim 16, wherein total amount of time for injection and substantial recovery of the human subject is within 30 minutes.

* * * * *